United States Patent [19]

Seshimoto

[11] Patent Number: 4,517,071
[45] Date of Patent: May 14, 1985

[54] IONIC ACTIVITY MEASURING DEVICE

[75] Inventor: Osamu Seshimoto, Asaka, Japan

[73] Assignee: Fuji Photo Film Co., Ltd., Japan

[21] Appl. No.: 413,087

[22] Filed: Aug. 30, 1982

[30] Foreign Application Priority Data

Sep. 17, 1981 [JP] Japan ................. 56-146730

[51] Int. Cl.³ ............................. G01N 27/46
[52] U.S. Cl. ................... 204/419; 204/1 T;
204/400; 324/158 F; 324/452
[58] Field of Search ............ 204/1 T, 416, 417, 418,
204/419; 324/158 F, 452, 453, 459, 464; 422/55
R, 58, 100

[56] References Cited

U.S. PATENT DOCUMENTS

| 4,020,830 | 5/1977 | Johnson et al. | 204/418 |
| 4,053,381 | 10/1977 | Humblen et al. | 204/416 |
| 4,180,771 | 12/1979 | Guckel | 204/418 |
| 4,184,936 | 1/1980 | Paul et al. | 204/416 |
| 4,273,639 | 6/1981 | Gottermeier | 204/416 |
| 4,305,802 | 12/1981 | Koshiishi | 204/419 |

FOREIGN PATENT DOCUMENTS 0023156 1/1981 European Pat. Off. ............ 204/416

Primary Examiner—Winston A. Douglas
Assistant Examiner—Terryence Chapman
Attorney, Agent, or Firm—Gerald J. Ferguson, Jr.;
Joseph J. Baker

[57] ABSTRACT

An ionic activity measuring device comprising a substrate provided with at least one opening for receiving a terminal made of a metal layer or a metal layer and a water insoluble metal salt layer, an ion selecting layer positioned on or in the substrate, and at least one liquid receiving hole for bringing liquid into contact with the ion selecting layer at the point vertically aligning with the opening in the substrate. The liquid receiving hole is formed in a porous bridge positioned on the ion selecting layer or on a bridge supporting material which is discrete from the ion selecting layer, or is formed in the substrate. The substrate may be a flexible film, and the device may further comprise a film feeding housing provided with a shaft for feeding the film and a film receiving housing provided with a wind-up shaft.

12 Claims, 14 Drawing Figures

FIG.I
PRIOR ART
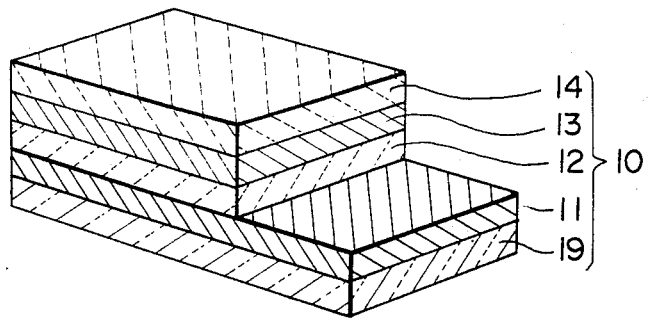
FIG.2
PRIOR ART
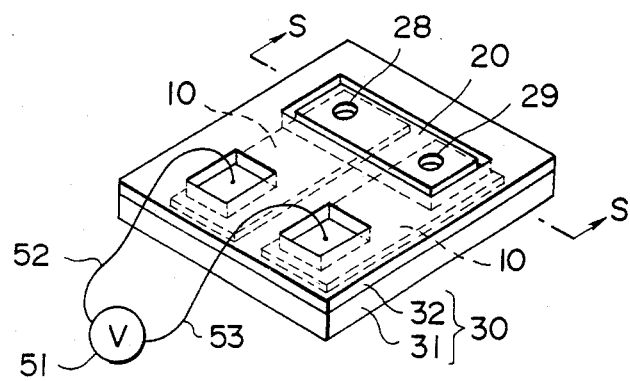
FIG.3
PRIOR ART
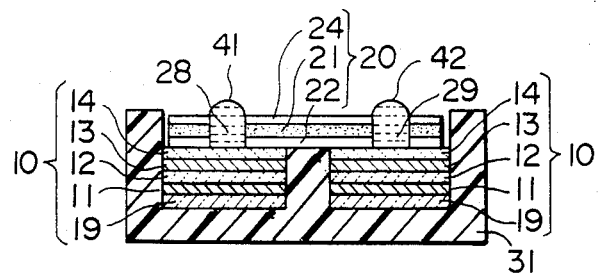

IONIC ACTIVITY MEASURING DEVICE

BACKGROUND OF THE INVENTION

1. Field of the Invention

This invention relates to a device for measuring ionic concentration or ionic activity, and more particularly to an ionic activity measuring device useful for potentiometric measurement of the concentration or ionic activity of an ion contained in specimens such as water, body fluids (for example, whole blood, blood plasma, blood serum, urine and the like), and aqueous solutions (for example, service water, factory waste water, river water, rain water, wine, beer and the like).

2. Description of the Prior Art

Generally, from the clinical or industrial point of view, it is important to selectively measure the concentration or the ionic activity of an inorganic ion, for example $K^+$, $Na^+$, $Ca^{2+}$, $Cl^-$ or $HCO_3^-$, contained in body fluids or aqueous solutions. For this purpose, it has been proposed to use a wet type ion selecting electrode.

The conventional wet type ion selecting electrode is in the form of a needle or a bar and dipped in a specimen such as body fluid each time it is used for measurement. Therefore, the electrode of this type must be appropriately maintained, washed and conditioned after it is used for measurement. This adversely affects the service life of the electrode and causes the electrode to break easily, requiring troublesome electrode management and great expense. Furthermore, it is necessary to use a large amount (e.g. several hundreds of microliters or more) of a specimen for measurement because the electrode head must be dipped to a sufficient depth in the specimen contained in a vessel such as a cup. In view of these drawbacks of the wet type ion selecting electrode, it has been proposed in Japanese Unexamined patent Publication No. 52(1977)-142584 to stack four functional layers on a substrate and form a film-like dry type solid ion selecting electrode. To conduct measurement with the film-like solid electrode of this type, a very small amount (e.g. between 5 μl and 50 μl) of a specimen is applied to a predetermined position on the ion selecting layer of the solid electrode.

FIG. 1, a solid ion selecting electrode 10 comprises a metal layer 11, a water-insoluble metal salt layer 12, a reference electrolyte layer 13 and an ion selecting layer 14 sequentially stacked as the functional layers on a substrate 19. For example, the metal layer 11 is formed of silver, the water-isouble metal salt layer 12 is formed of silver chloride, and the reference electrolyte layer 13 is made by dispersing potassium chloride in a hydrophilic organic polymer binder.

It has also been proposed in Japanese patent application No. 55(1980)-92378 to use a film-like electrode comprising three stacked functional layer, in which the reference electrolyte layer 13 shown in FIG. 1 is omitted, and the ion selecting layer 14 consisting of organic materials is directly positioned on the water-insoluble metal salt layer 12. Further, Japanese Unexamined Patent Publication No. 48(1973)-82897 discloses film-like solid electrode comprising two stacked functional layers, in which the water-insoluble metal salt layer 12 and the reference electrolyte layer 13 shown in FIG. 1 are omitted, and an ion selecting layer 14 containing an ion exchange material is directly positioned on the metal layer 11.

In case the ion to be measured is $Cl^-$ and the electrode comprises a metal layer 11 made of silver and an insoluble metal salt layer 12 made of silver chloride, it is possible to position on the silver chloride layer a halogen ion-pervious coating layer made of, for example, cellulose acetate, polymethacrylic acid, polyacrylic acid, or poly(2-hydroxyethyl acrylate) employed in a halogen ion-pervious coating layer as disclosed in Japanese Unexamined Patnent Publication 55(1980)-89741. The halogen ion-pervious coating layer is also referred to herein as the ion selecting layer.

FIG. 2 is a schematic view showing a conventional ion measuring instrument comprising two film-like solid electrodes of the type shown in FIG. 1, as disclosed in U.S. Pat. No. 4,053,381. The conventional ion measuring instrument shown in FIG. 2 comprises film-like solid ion selecting electrodes 10 of the type shown in FIG. 1, which are fixed in a frame 31 so that they are electrically isolated from each other. A porous bridge 20 formed of a porous member extends over the film-like solid ion selecting electrodes 10. A potentiometer (or a potential indicator) 51 is connected to the metal layer 11 of the electrodes 10 by lead wires 52 and 53. When measurement is conducted with the instrument shown in FIG. 2, a specimen and a standard solution are dropped almost at the same time into liquid receiving holes 28 and 29 respectively, which are perforated through the bridge 20 positioned on the electrodes 10. The specimen and the standard solution then exhibit capillary phenomena and penetrate through the porous member of the bridge 20. When the specimen and the standard solution contact each other approximately at the center of the bridge 20 and ion transfer occurs, the difference in potential between the electrodes 10 is indicated on the potentiometer 51. By measuring the difference in potential, it is possible to determine the concentration or the activity of an ion contained in the specimen.

FIG. 3 is a sectional schematic view, taken along the line S-S in FIG. 2. Japanese Unexamined Patent Publication No. 55(1980)-20499 discloses a bridge 20 having a configuration as shown in FIG. 3 comprising a non-porous bottom substrate 22 (existing nearest to the solid ion selecting electrode), an intermediate porous layer 21, and a top non-porous hydrophobic layer 24 (existing farthest from the solid ion selecting electrode). The bridge 20 is formed as a flat three-layer laminate strip having the liquid receiving holes 28 and 29, into which solutions 41 and 42 are dropped.

To prevent the functional layers of the electrodes from being short-circuited at their ends due to the specimen or the standard solution bleeding out of the bridge 20, the bridge 20 is sealed from the electrodes at least at the circumferences of the liquid receiving holes 28 and 29.

The intermediate porous layer 21 is made, for example, of porous paper, a membrane filter, threads, a fabric or the like. The layer 21 absorbs the droplets 41 and 42 and causes them to contact each other, resulting in ion transfer. When droplets are applied to the liquid receiving holes 28 and 29, the droplets fill up the holes, form a large "lid" on the top layer 24, and are then absorbed into the layer 21 in five to 30 seconds. The liquids diffuse through the bridge 20 and come into contact with each other at approximately equal distances from the liquid receiving holes 28 and 29, i.e. approximately at the center of the bridge 20. In this way, ion transfer becomes possible, and potential develops between the electrodes 10. Further, sufficient liquids to fill up the liquid receiving holes 28 and 29 are not absorbed into the layer 21 but remain in the holes 28 and 29.

Other examples of the materials preferable as the intermediate porous layer are described in Japanese Unexamined Patent Publication No. 52(1977)-142584.

The conventional ion measuring instrument described above can measure the ionic concentration or the ionic activity by use of small amounts of a specimen and a standard solution. Further, since the instrument is disposable, it does not require maintenance, cleaning and conditioning of the electrodes and thus is easy to handle. However, the conventional instrument is disadvantageous in that, because it is thrown away after being used for measurement, the expensive metals such as Ag and metal salts such as AgCl contained in the electrodes are wasted each time measurement is conducted. Further, the ion selecting layer described above consists of an organic compound (ion carrier) possessing ion selecting capability, a carrier solvent and an organic polymer binder. As the ion carrier, an ion exchange material, a crown ether compound or an antibiotic (e.g. Valinomycin capable of selecting potassium ion, or the like) is used. However, when the ion carrier such as Valinomycin is recovered together with the metal such as Ag and the metal salt such as AgCl after measurement, the ion carrier will attach to the human body during the recovering operation and adversely affects the human body.

SUMMARY OF THE INVENTION

The primary object of the present invention is to provide an improved ionic activity measuring device.

Another object of the present invention is to provide an ionic activity measuring device in which the expensive metal such as Ag and the metal salt such as AgCl can be used repeatedly for many measuring operations.

The specific object of the present invention is to provide an ionic activity measuring device from which the expensive metal such as Ag and the metal salt such as AgCl can be easily recovered without any risk of the human body coming into contact with the harmful ion selecting substance.

The ionic activity measuring device in accordance with the present invention comprises a substrate provided with at least one opening for receiving at least one terminal, an ion selecting layer supported by said substrate, and a means for bringing a specimen or a specimen and a reference solution (standard solution) into contact with said ion selecting layer at the point or points vertically aligning with said at least one opening in said substrate. The terminal contains at least a metal such as Ag, preferably a metal such as Ag and a water-insoluble salt of said metal such as AgCl which contact each other (in the latter case, the terminal is called the terminal-like solid reference electrode or the terminal-like solid single electrode). The terminal may be of any configuration insofar as it can constitute the solid ion selecting electrode as described above when contacted with the ionic activity measuring device, which contains the ion selecting layer, from the opening of the substrate. The terminal containing a metal such as Ag is inserted into the opening provided in the substrate when measurement is conducted, and withdrawn from the opening when measurement is over. Accordingly, the terminal can be used repeatedly for many measuring operations, and the metal such as Ag can be easily recovered from the terminal without any risk for the human body to be adversely affected by the materials contained in the ion selecting layer.

In the present invention, the solid electrode may have a construction similar to that generally called half cell or single electrode.

The present invention will hereinbelow be described in further detail with reference to the accompanying drawings.

BRIEF DESCRIPTION OF THE DRAWINGS

FIGS. 1–3 show the prior art

DESCRIPTION OF THE PREFERRED EMBODIMENTS

Figure 4:
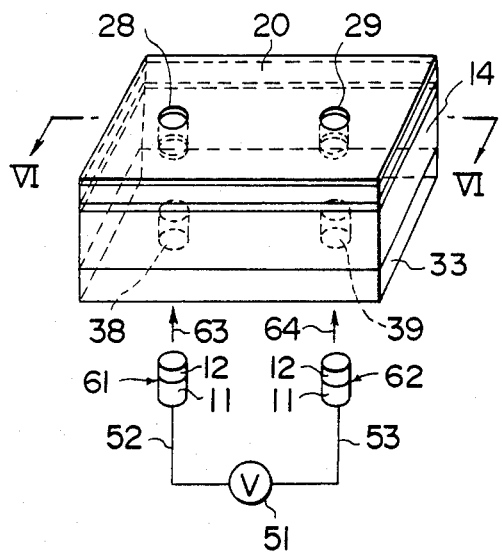
FIG. 4 is a perspective view showing an embodiment of the ionic activity measuring device in accordance with the present invention.

Preferred embodiments of the present invention will now be described below with reference to FIGS. 4 to 14, wherein like reference numerals designate like or corresponding parts throughout.

Figure 5:
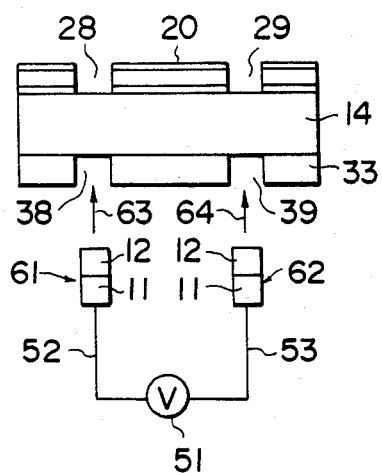
FIG. 5 is a sectional view taken along the line VI—VI in FIG. 4.

In FIGS. 4 and 5 showing an embodiment of the ionic activity measuring device in accordance with the present invention, an ion selecting layer 14 is positioned on a substrate 33 provided with two terminal receiving openings 38 and 39. On the ion selecting layer 14 is positioned a bridge 20 formed of a porous member or the like provided with two liquid receiving holes 28 and 29 for holding a specimen and a standard solution respectively dropped onto the ion selecting layer 14. Terminals 61 and 62 which are brought into contact with the ion selecting layer 14 when the ionic concentration or the ionic activity is measured consist of a metal layer 11 and a water-insoluble metal salt layer 12 containing the same metal as that forming the metal layer 11. The water-insoluble metal salt layer 12 can be brought into direct contact with the ion selecting layer 14. In the terminals 61 and 62 respectively, the metal layer 11 may be made for example of Ag, and the water-insoluble metal salt layer 12 may be formed of AgCl.

To measure the ionic concentration or the ionic activity by use of the device shown in FIGS. 4 and 5, lead wires 52 and 53 of a potentiometer 51 are connected to the metal layers 11 of the terminals 61 and 62. The terminals 61 and 62 are then moved in the directions of the arrows 63 and 64 into the openings 38 and 39 of the substrate 33 and contacted with the ion selecting layer 14 at an appropriate pressure. Thereafter, a specimen and a standard solution are dropped into the liquid receiving holes 28 and 29, respectively. In this way, it is possible to determine the ionic concentration or the ionic activity by measuring the difference in potential indicated on the potentiometer (or the potential indicator) 51 when the specimen and the standard solution diffuse from the holes 28 and 29 through the bridge 20 and contact each other. After the measurement is finished, the terminals 61 and 62 are withdrawn from the openings 38 and 39 of the substrate 33, and the section of the device containing the waste ion selecting layer 14 is discarded or sent to a process for recovering the ion selecting material. To further conduct the measurement, another section of the device containing a new ion selecting layer 14 is used in the same way as described above.

In the embodiment shown in FIGS. 4 and 5, the terminals containing an expensive metal such as Ag can be used repeatedly and, therefore, the cost for measuring the ionic activity is reduced. Further, since the ion selecting layer and the metal layer are formed separately from each other, it is easy to recover the ion selecting material and the expensive metal such as Ag.

In FIGS. 4 and 5, the terminals 61 and 62 respectively are formed of the metal layer 11 and the water-insoluble metal salt layer 12 containing the same metal as in the metal layer 11. However, it is also possible to position a reference electrolyte layer on the water-insoluble metal salt layer 12.

Figure 6:
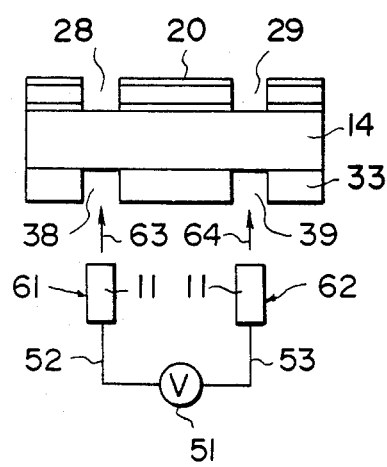
FIG. 6 is a sectional view showing another embodiment of the device in accordance with the present invention.

FIG. 6 shows another embodiment of the ionic activity measuring device in accordance with the present invention. In FIG. 6, terminals 61 and 62 respectively are formed only of a metal layer 11, which can directly be contacted with an ion selecting layer 14. The metal layer 11 may be made of Ag, Pt, Cu or the like. The device shown in FIG. 6 can be used for measurement in the same way as the device shown in FIGS. 4 and 5.

Figure 7:
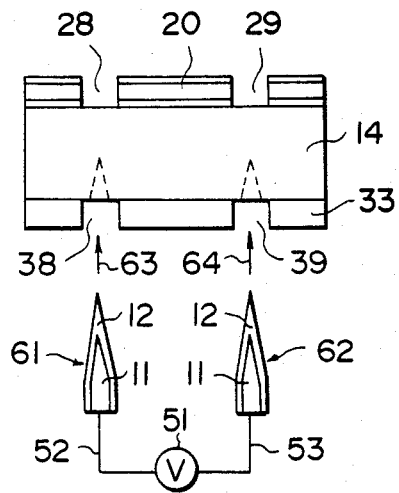
FIG. 7 is a sectional view showing a further embodiment of the device in accordance with the present invention.

FIG. 7 shows a further embodiment of the ionic activity measuring device in accordance with the present invention. In FIG. 7, terminals 61 and 62 have a needle-like form and are inserted into an ion selecting layer 14 when used for measurement. Therefore, it is preferable that the ion selecting layer 14 be made sufficiently thick to receive the needle-like terminals 61 and 62. Although the terminals 61 and 62 shown are respectively formed of a metal layer 11 and a water-insoluble metal salt layer 12, they may also be formed only of a metal layer 11.

Figure 8:
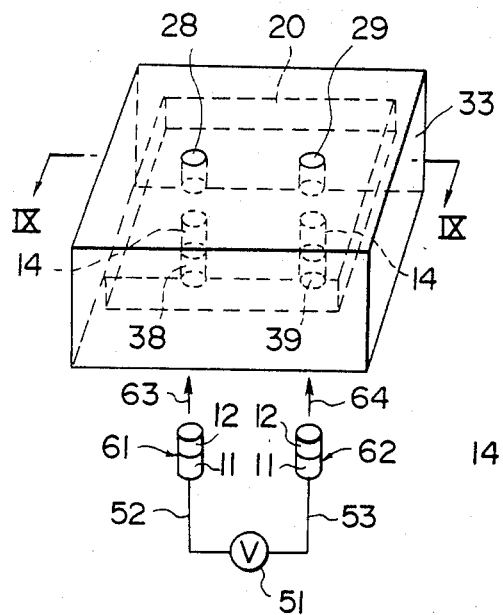
FIG. 8 is a perspective view showing a still further embodiment of the device in accordance with the present invention.
Figure 9:
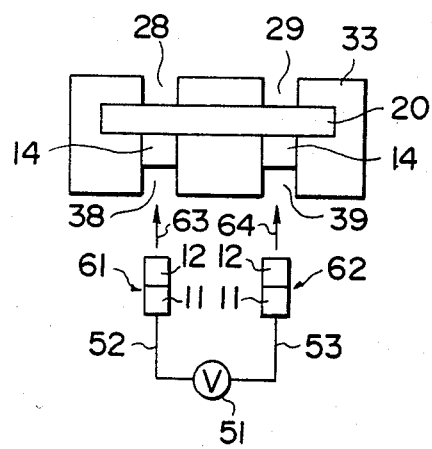
FIG. 9 is a sectional view taken along the line IX—IX in FIG. 8, and FIGS. 10 to 14 are sectional views showing various other embodiments of the device in accordance with the present invention.

In FIGS. 8 and 9 showing a still further embodiment of the device in accordance with the present invention, a bridge 20 is built in a substrate 33, and an ion selecting layer 14 is positioned at each of terminal receiving openings 38 and 39. Accordingly, this embodiment eliminates the problem in the conventional ion measuring instrument with regard to the difficulty in bonding the ion selecting layer 14 containing an ion carrier solvent to the bridge 9.

Figure 10:
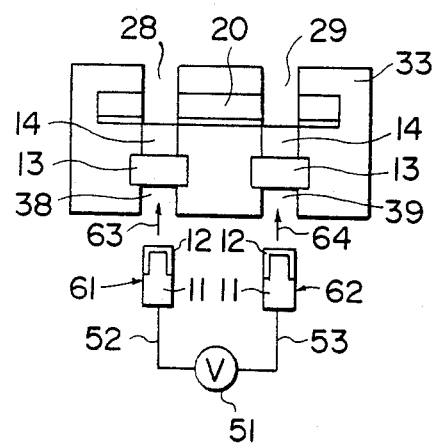

In FIG. 10 showing another embodiment of the device in accordance with the present invention, reference electrolyte layers 13 consisting of a porous member impregnated with an electrolyte such as KCl are positioned at terminal receiving openings 38 and 39 so that the electrodes 61 and 62 can be contacted with the reference electrolyte layers 13. In this embodiment, it should be noted that the terminals 61 and 62 may be shaped to a needle-like form as shown in FIG. 7 and may be inserted in the reference electrolyte layers 13.

Figure 11:
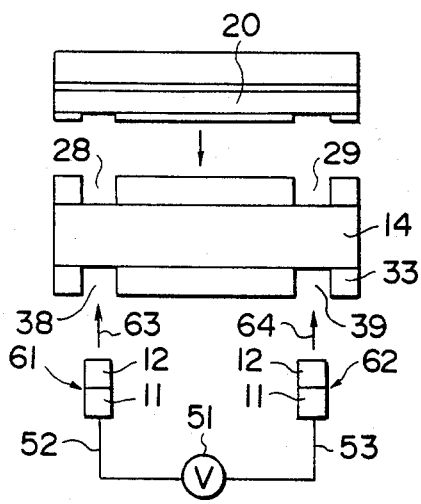

FIG. 11 shows another embodiment of the device in accordance with the present invention, in which a bridge 20 is formed separately from an ion selecting layer 14. When measurement is conducted with the device shown in FIG. 11, a specimen and reference solution are dropped into liquid receiving holes 28 and 29 respectively, and then the bridge 20 is placed above the ion selecting layer 14 to develop ion transfer between the specimen and the standard solution. Then, a potential difference between metal layers 11 of terminals 61 and 62 contacted with the ion selecting layer 14 is read out from a potentiometer 51.

In the device shown in FIG. 11, the point of time when the specimen is dropped into the hole 28 and the point of time when the standard solution is dropped into the hole 29 may differ from each other. Further, it is possible to conduct measurement with high accuracy because the liquid receiving holes 28 and 29 are closed by the bridge 20 to prevent the specimen and the standard solution from evaporating.

Figure 12:
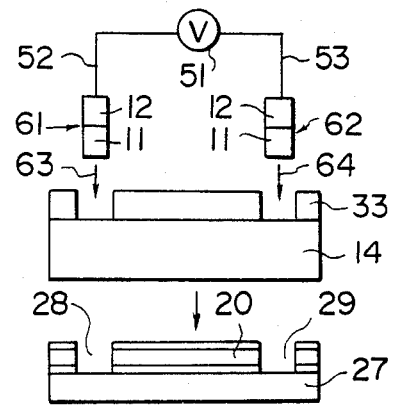

FIG. 12 shows another embodiment of the device in accordance with the present invention, in which an ion selecting layer 14 and a bridge 20 are formed separately from each other like the device shown in FIG. 11. In FIG. 12, the bridge 20 provided with liquid receiving holes 28 and 29 is positioned on a bridge supporting material 27, and the ion selecting layer 14 mounted on a substrate 33 is brought into contact with the bridge 20 from above when the measurement is conducted. The device shown in FIG. 12 is advantageous in that the liquid receiving holes 28 and 29 are closed by the ion selecting layer 14 to prevent the specimen and the standard solution from evaporating during measurement. Further, since electrodes 61 and 62 are brought into contact with the ion selecting layer 14 from above, it is easy to conduct measurement.

Figure 13:
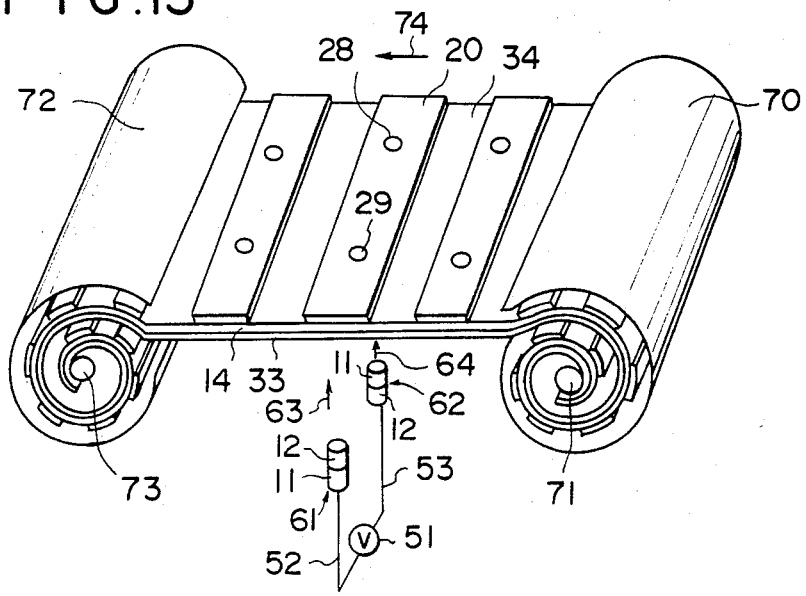

FIG. 13 shows another embodiment of the device in accordance with the present invention, in which an ion selecting electrode 14 is positioned on flexible substrate 33, and a plurality of bridges 20 are positioned on the ion selecting layer 14 to form an ionic activity measuring film 34. During storage, the film 34 is wound around a rotation shaft 71 in a patrone-like feed housing 70 as shown. When the film 34 is used for measurement, the leading edge thereof is fixed to a wind-up shaft 73 in a film receiving housing 72, and the film 34 is moved in the direction of the arrow 74 by turning the wind-up shaft 73 until openings 38 and 39 in the substrate 33 align with the terminals 61 and 62. Thereafter, a specimen and a standard solution are dropped into liquid receiving holes 28 and 29 of the bridge 20, and the terminals 61 and 62 are brought into contact with the ion selecting layer 14 through the openings 38 and 39 of the substrate 33, thereby to measure the ionic concentration or the ionic activity.

In FIG. 13, when the measurement is finished, the terminals 61 and 62 are withdrawn from the openings 38 and 39 of the substrate 33, and the ionic activity measuring film 34 is moved in the direction of the arrow 75 until the next bridge 20 is positioned above the terminals 61 and 62 to further conduct measurement. After all bridges 20 of the film 34 are used for measurement, the film 34 is completely contained in the film receiving housing 72.

In the embodiment of FIG. 13, the ion selecting layer 14 is contained in the feed housing 70 before it is used for measurement, and is accommodated in the film receiving housing 72 after measurement. Accordingly, it is easy to handle the ion selecting layer 14 before and during the measurement and to treat the layer 14 after measurement.

Moreover, in FIG. 13, the measurement of the ionic activity can further be facilitated if the measurement and the transfer of the ionic activity measuring film are appropriately associated with each other, for example, by using an electrically-driven winder of the type normally used in a camera. It is also possible to provide two or more pairs of terminals and position different ion selecting layers in a manner corresponding to respective pairs of terminals, thereby to measure the concentrations or activities of different ions contained in a specimen simultaneously by one liquid-applying operation.

Figure 14:
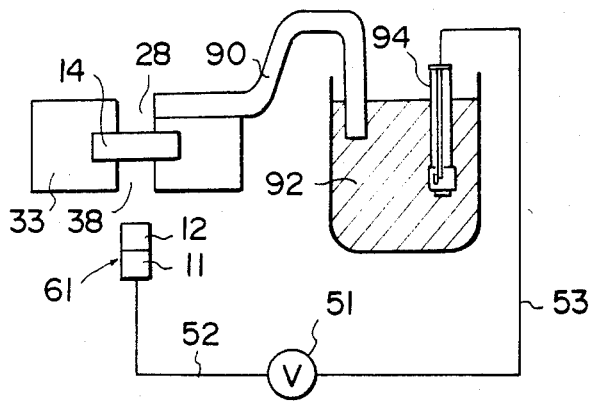

FIG. 14 shows another embodiment of the device in accordance with the present invention, which is suitable for conducting absolute measurement of the ionic concentration or the ionic activity. In FIG. 14, an ion selecting layer 14 is positioned in the interior of a substrate 33, a liquid receiving hole 28 is positioned above the ion selecting layer 14, and a terminal receiving hole 38 is positioned below the ion selecting layer 14. The liquid receiving hole 28 is communicated with a 1N KCl solution 92 by an agar bridge 90 containing KCl or the like. A standard electrode 94 is dipped in the KCl solution 92, and a potentiometer 51 is connected between the standard electrode 94 and a terminal 61. When the absolute measurement of the ionic concentration or the ionic activity is conducted with the device shown in FIG. 14, a specimen is dropped into the liquid receiving hole 28, and then the terminal 61 is brought into contact with the ion selecting layer 14 through the opening 38.

I claim:

1. An ionic activity measuring device comprising a substrate provided with at least one opening for receiving at least one terminal, said at least one terminal consisting of a metal layer and a water-insoluble layer made of a salt of the same metal as that forming said metal layer, an ion selecting layer supported by said substrate, and a means for bringing liquid into contact with said ion selecting layer at the point vertically aligned with said at least one opening in said substrate.

2. A device as defined in claim 1 wherein said means for bringing liquid into contact with said ion selecting layer is at least one liquid receiving hole positioned on said ion selecting layer.

3. A device as defined in claim 2 wherein said at least one liquid receiving hole is formed in a porous bridge positioned on said ion selecting layer.

4. A device as defined in claim 2 wherein said at least one liquid receiving hole is formed in said substrate.

5. A device as defined in claim 4 further comprising a porous bridge adapted to close said at least one liquid receiving hole from above.

6. A device as defined in claim 1 wherein said means for bringing liquid into contact with said ion selecting layer is at least one liquid receiving hole positioned on a supporting material which is discrete from said ion selecting layer and which is opposed to the surface of said ion selecting layer.

7. A device as defined in claim 6 wherein said at least one liquid receiving hole is formed in a porous bridge positioned on said supporting material.

8. A device as defined in claim 1 wherein said at least one terminal is shaped in needle-like form and said ion selecting layer is adapted to receive the pointed tip of said needle-like terminal.

9. A device as defined in claim 1 wherein said ion selecting layer is shaped to fit in to the interior of said at least one opening in said substrate and positioned therein.

10. A device as defined in claim 1 further comprising a reference electrolyte layer positioned in contact with said ion selecting layer at said opening in said substrate, said reference electrolyte layer capable of being contacted with said terminal.

11. A device as defined in claim 1 wherein said substrate is in the form of a flexible film, said ion selecting layer is positioned on said substrate over the entire length thereof, a plurality of said means for bringing liquid into contact with said ion selecting layer are positioned on said ion selecting layer, and said device further comprises a film feeding housing provided with a film feeding shaft and a film receiving housing provided with a film wind-up shaft.

12. A device as defined in claim 1 wherein said substrate is provided with one opening for receiving the terminal, said means for bringing liquid into contact with said ion selecting layer is a liquid receiving hole formed in said substrate, said liquid receiving hole is communicated with a standard solution contained in a vessel by a bridge, and a potential indicating means is connected between said terminal and a standard electrode dipped in said standard solution.

* * * * *